United States Patent [19]

Arlinghaus et al.

[11] Patent Number: 5,126,399

[45] Date of Patent: Jun. 30, 1992

[54] METHODS AND COMPOSITIONS FOR THE PREPARATION AND USE OF SITE-DIRECTED IMMUNOLOGIC REAGENTS

[75] Inventors: Ralph B. Arlinghaus, Bellaire; James T. Sparrow, Houston, both of Tex.

[73] Assignees: Board of Regents, The University of Texas System, Austin; Baylor College of Medicine, Houston, both of Tex.

[21] Appl. No.: 368,713

[22] Filed: Jun. 20, 1989
(Under 37 CFR 1.47)

Related U.S. Application Data

[63] Continuation-in-part of Ser. No. 368,708, Jun. 19, 1989, Pat. No. 4,973,638, which is a continuation-in-part of Ser. No. 858,216, Apr. 30, 1986, abandoned.

[51] Int. Cl.$^5$ .................. C08G 63/48; C08G 63/91; A01N 37/18
[52] U.S. Cl. ...................... 525/54.1; 514/2; 514/13; 514/14; 514/15; 514/16
[58] Field of Search ............... 525/54.1; 424/2; 514/2, 514/13, 14, 15, 16

[56] References Cited

FOREIGN PATENT DOCUMENTS

WO87/07616  12/1987  European Pat. Off. .
EP250253    12/1987  European Pat. Off. .
WO87/06594  11/1987  PCT Int'l Appl. .
WO88/00471   1/1988  PCT Int'l Appl. .

OTHER PUBLICATIONS

Milich "Nonoverlapping T and B Cell Determinants on an Hepatitis B Surface Antigen Pre-S(2) Region Synthetic Peptide", J. Exp. Med., vol. 164, 532–547.

Maddon et al., "The T4 Gene Encodes the AIDS Virus Receptor and is Expressed in the Immune System and the Brain", Cell, vol. 47, 333–348, Nov. 7, 1986.

Modrow et al., "Computer–Assisted Analysis of Envelope Protein Sequences of Seven Human Immunodeficiency Virus Isolates: Prediction of Antigenic Epitopes in Conserved and Variable Regions", J. of Virology, Feb. 1987 pp. 570–578.

Merrifield, R. B. (1969), "Solid–phase Peptide Synthesis", Adv. Enzymology, 32:221.
Atherton et al. (1975), J. Amer. Chem. Soc., 97:6584.
Arshady et al. (1979), "Easily Prepared Polar Support for Solid Phase Peptide and Oligonucleotide Synthesis", J. C. S. Chem. Comm., 425.
Dreesman et al. (1982), Nature, 295:158.
Lerner et al. (1981), Proc. Natl. Acad. Sci. USA, 78:3403.
Prince et al. (1982), Proc. Natl. Acad. Sci. USA, 79:579.
Sanchez et al. (1982), Intervirology, 18:209.
Reddy et al. (1983a), Proc. Natl. Acad. Sci. USA, 80:3623; Reddy et al. (1983b), Proc. Natl. Acad. Sci. USA, 80:7372.
Sparrow, J. T. (1976), J. Organ. Chem., 41:1350.
Liu et al. (1979), Biochemistry, 79:690.
Van Regenmortel et al. (1986), Annals Inst. Pasteur, 137E:497.
Krzych et al. (1988), Faseb J., 2:141.
Manning, M. (1968), J. Am. Chem. Soc., 90:1348.
Helpern et al. (1980), Synthetic Comm., 10:569.
Tesser et al. (1975), Int. J. Peptide Protein Res., 7:295.
Mitchell et al. (1978), J. Org. Chem., 43:2845.

(List continued on next page.)

Primary Examiner—Nathan M. Nutter
Attorney, Agent, or Firm—Arnold, White & Durkee

[57] ABSTRACT

Disclosed are peptidyl-resin conjugates made up of an immunogenic/antigenic peptide conjugated to a polyamide resin, wherein the peptide incorporates a helper T-cell epitope. The inclusion of a T-cell epitope in this peptide sequence provides particular benefits in the preparation of site-directed reagents intended as immunogens. In exemplary studies, a synthetic peptide predicted from Abelson murine leukemia virus abl oncogene (residues 389–403) was synthesized with a T-cell active epitope of 7 amino acids placed at its N-terminus (T-abl-resin). The T-abl-resin construct was found to greatly stimulate the immune response giving significantly higher specific antibody titers than abl-resin controls.

9 Claims, 3 Drawing Sheets

OTHER PUBLICATIONS

Kloetzer et al. (1985), *Virology,* 140:230–238.
Laemmli (1970), *Nature,* 227:680–685.
Livingstone et al. (1987), *Ann. Rev. Immunol.,* 5:477.
International Search Report.
Takeyama et al. (1989), *Chemical Abstracts, 111:132012a.*
Kanda et al. (1986), *Chemical Abstracts,* 106:82707e.
Takeyama et al. (1989), *Chemical Abstracts,* 111:21749b.
Milich et al. (1986), *J. Exp. Med.,* 164:532–547.
Chanh et al. (1986), *Embo Jrnl.,* 5(11):3065–3071.
Rothbard (1987), *Nature,* 330:106–107.
Leclerc et al. (1987), *Eur. J. Immunol.,* 17:269–273.
Francis et al. (1987), *Nature,* 330:168–170.
Kennedy et al. (1987), *Jrnl. Biol. Chem.,* 262(12):5769–5774.
Francis et al. (1987), *Immunol.,* 61:1–6.
Good et al. (1987), *Science,* 235:1059–1062.

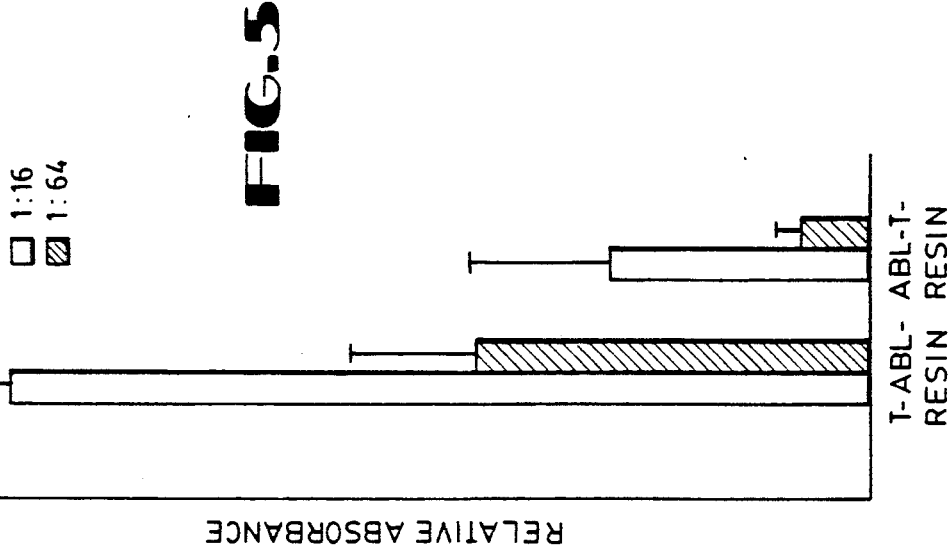

METHODS AND COMPOSITIONS FOR THE PREPARATION AND USE OF SITE-DIRECTED IMMUNOLOGIC REAGENTS

The government may own certain rights in the present invention pursuant to NIH grant 2RO1-HL30064.

The present application is a continuation-in-part of U.S. Ser. No. 368,708, filed Jun. 19, 1989, now U.S. Pat. No. 4,973,638, which was a continuation-in-part of U.S. Ser. No. 858,216, filed Apr. 30, 1986, now abandoned.

1. Field of the Invention

The present invention relates to the synthesis and use of synthetic peptides and proteins to induce an immune response in animals. In particular aspects, the invention concerns the preparation and use of immunogenic and-/or antigenic peptides linked to polyamide resins which incorporate T cell determinants.

2. Description of the Related Art

Solid phase peptide synthesis is a valuable tool for investigating the structure and mechanism of action of proteins. Most such synthetic methods involve the use of a cross-linked polystyrene based resin as the solid phase to which the peptide is anchored during assembly, usually through a linker molecule. Assembly is accomplished by a repetitive cycle of adding a protected amino acid to the solid phase, selectively removing (deprotecting) a protective group on that amino acid, and adding additional suitable protected amino acids (1).

Cross-linked, polystyrene based resins are commonly used as supports in solid phase peptide synthesis. Unfortunately, their relatively hydrophobic character in comparison to the polar organic media required to solubilize reactants can be problematic in peptide chain assembly. Such media may freely solvate the growing peptide, yet incompletely swell the polystyrene matrix. Within the polymer lattice, impaired diffusion of reagents and steric hindrance can contribute to lowered efficiency during coupling cycles, which, on a repeated basis, lowers final yields appreciably. During the early stages of assembly, when the resin to peptide mass ratio is high and the physical properties of the support dominate, this lowered efficiency is particularly acute.

These shortcomings led to the development of a cross-linked, polydimethylacrylamide based support which is highly polar in character and is freely permeated by the requisite solvents for peptide synthesis (2,3). The polyamide resin, as the amino methyl derivative, can accommodate synthetic schemes incorporating alternate protection strategies through selection of the appropriate linker molecule, which links the C-terminal residue to the support. The peptide or protein thus synthesized, which will be referred to throughout the present disclosure as a "protide", can be used in a number of investigative applications.

Of particular interest to the present invention is the use of the protide as an immunogen. It has previously been demonstrated that synthetic peptides analogous to sequences contained in viral encoded proteins have proven useful for identification of native antigen determinants associated with such proteins. Several laboratories have reported studies on the antigenic activity of various HBsAg synthetic peptides (4-6). The induction of an antibody response to HBsAg, using such peptides, proved to be relatively weak, but could be enhanced through coupling of peptides to a carrier protein prior to immunization (5,7).

Because the prediction of potential antigenic determinants of immunogenic proteins based on primary sequences analysis is not exact, the identification of putative epitopes through trial and error can be laborious. A method which involves the delineation of native antigenic sequences with synthetic peptides which does not require purification of the synthetic peptide and coupling of the peptide to carrier proteins offers significant advantages.

Polyamide resins have also been employed as a solid phase for peptide and protein synthesis (8). In these studies, polyamide resins were prepared by cross-linking a dimethylacrylamide monomer by co-polymerization with a functional monomer in an aqueous solution, organic emulsification, followed by isolation of the resultant beads. These beads were used as a solid phase for synthesizing peptides. These conjugates were employed directly in immunoassays and immunization protocols by these investigators without separating the peptide or protein from the resin and subsequent purification.

Peptide-conjugated polyamide resin beads, such as the foregoing, have been shown to provide some advantages over other immunogens or antigens, both in terms of ease of preparation and use, and by providing a site-directed immunologic capability. Unfortunately, while it provides certain advantages it is believed that this technology never the less suffers from significant drawbacks, for example, in terms of the level of the induced immune response and the breadth of the responses in an outbred population of recipients.

For the foregoing and other reasons there is currently a significant need for improved, site-directed immunologic reagents, having one or more advantages over previous immunologic reagents. There is a particular need to develop improved methods and compositions for the preparation and use of resin-bound peptides, that will address one or more of the disadvantages of the prior art, for example, that addresses the often poor immunogenicity or antigenicity associated with short or poorly B-cell reactive peptides or proteins.

SUMMARY OF THE INVENTION

The present invention addresses one or more of the foregoing or other disadvantages in the art by providing an improved peptide-resin conjugate for use in immunological applications ranging from immunization protocols to immunoassays and perhaps even vaccines.

In a general and overall sense, the invention concerns the preparation of improved peptide-resin conjugates which incorporate helper T-cell reactive epitopes. These constructs can be employed advantageously in a variety of immunologic procedures which employ immunogenic and/or antigens proteins or peptides. A particular advantage of the peptide-resin conjugate of the present invention is the ability to provide a "site-directed" immunologic capability wherein antibodies are generated or targeted against a particular, selected site. Thus, it will generally be the case that peptide-resin conjugates of the invention will incorporate, in addition to the helper T-cell epitope, a second epitope against which the desired antibody is to be generated or targeted. This second epitope will generally be considered a "B-cell" epitope in that B-cells are the source of specific antibody production. Of course, where one desires to generate or target site-directed antibodies against a helper T-cell epitope itself, a separate B-cell epitope on the resin-conjugated peptide or protein will not be required in order to realize certain advantages in accordance with the invention.

The present invention therefore takes advantage of the observation that the incorporation of a helper T-cell epitope into a peptide bearing a B-cell reactive (i.e., immunogenic) epitope will substantially increase the immunogenicity of the targeted epitope. The invention is thus predicated at least in part on the inventors' finding that the application of this technology to resin-bound peptide conjugates will provide substantial benefits in terms of the immunogenic capability of the resultant hybrid conjugate—benefits of a magnitude that could not have been predicted based on a consideration of previous technology.

As used herein, the term "peptide" is intended to refer generally to both peptides or proteins, and is not intended to imply any size restriction on the amino acid polymer. However, due to the nature of the invention and in that one of its most important applications being site-directed immunization, it will generally be the case that the peptides employed will be relatively short, on the order of about 20 to 50 amino acids in length. Similarly, the term "protide", as used herein, refers to both peptides and proteins which are synthesized according to the method of the present invention, whether unprotected or not. Protide synthesized on resins such as polyamide resins can be used to induce an immunogenic response in a mammal without being separated from the resin and purified.

While in preferred aspects the invention employs the use of polyamide resins with an appropriate crosslinking group for forming conjugates in accordance herewith, the invention is not limited to the use of polyamide resins. In general, the use of any resin known in the art to be useful for conjugation to immunogenic or antigen peptides can be used and still realize certain benefits in accordance herewith. Useful resins include but are not limited to resins such as polystyrene, polyethylene glycol, polydextran (hydroxypropylated), and the like. The more preferred resins will be those that will swell in an aqueous buffer solutions such that water molecules will be able to penetrate to the interior regions of the resin, thereby exposing the linked protide.

In certain embodiments of the invention, the resin is employed for direct synthesis of the peptide onto a solid phase resin "bead" to form the peptidyl-resin conjugate. In these methods, a resin suitable for solid phase peptide synthesis, such as a polyamide resin bead, is first selected. Next, a peptide bearing the epitope to be targeted, and which includes a helper T-cell reactive epitope, is synthesized onto the resin to provide the desired conjugate. The position of the T-cell epitope is important. The inventors have found that the T-cell epitope should preferably be positioned along the peptide at a point distal to the end of the peptide attached to the resin.

While the approach of synthesis directly onto the peptide will generally be preferred, there's no reason why, where desired, the peptides or proteins, could be obtained by other means and resin conjugated separately, e.g., by chemical cross-linking.

As noted, a principal feature of the invention is the inclusion of a helper T-cell reactive epitope in the peptidyl portion of the conjugate or protide. Generally, helper T-cell reactive epitopes are identified as determinants that are recognized by helper T-cells, in contrast to those recognized only by B-cells. B-cell epitopes, on the contrary, are defined by their ability to stimulate B-cells, and be recognized by antibodies. Helper T-cell epitopes or determinants can typically be identified by assays known in the art, e.g., assays for proliferative responses of T-cells or assays that measure the production of interleukin-2 (IL-2).

A number of helper T-cell reactive epitopes have been identified from a variety of protein derivations, including regions from proteins such as the staph. aureus nuclease protein (14); foot-and-mouth disease virus, VP1 protein, (15); T6 peptide, beta galactosidase (16); malaria parasite circumsporozoite protein, Th2R, (17); human immunodeficiency virus (HIV) gp120, env T1 (18); HIV gp12, env T2 (19); and hepatitis B surface antigen (subtype ayw) (20). The present invention contemplates that T-cell reactive epitopes useful in the practice of the invention can be identified by reference to accepted immunological assays, such as, in particular, by activation of T-cells as described in the T-cell proliferation assay of Milich et al. (20).

By way of theory and not limitation, it is believed that the stimulation observed upon immunogenic challenge in the practice of aspects of the invention is based on the functionality of helper T-cells in supporting the growth of B-cells. Specifically, T-helper cells after activation by a T-cell epitope produce growth factors such as B-cell growth factor and B-cell differentiation factors that favor the production of mature B-cells that produce useful antibodies. However, the activation of other cells of T-cell lineages, such as T suppressor cells or T cytotoxic cells, would not be desired due to their propensity for the release of cytokines that may limit B-cell reactivity. For this reason, it is important to distinguish T helper from T suppressor and T cytotoxic epitopes.

In certain embodiments of the invention, peptide-resin conjugates incorporating B-cell and helper T-cell reactive epitopes will find particular applicability in laboratory animal immunizations (e.g., pig, rat, mouse, rabbit, etc.), for use, e.g., in either the generation of polyclonal antisera or for immunological programming of lymphoid cells for hybridoma development. Due to their generally highly immunogenic nature, it is believed that protides in accordance with the invention will generally provide significant advantages in the foregoing uses, by eliciting a high antibody titer and/or a high percentage of positive hybridoma clones.

Accordingly, to take advantage of the nature of the immunogenic reagents described herein, in certain embodiments the invention concerns methods for inducing an immune response in a mammal such as one of the foregoing. This aspect of the invention involves first preparing a peptidyl-resin conjugate which includes an immunogenic peptide conjugated to a polyamide resin, wherein the peptide incorporates a helper T-cell epitope. Next, the method involves immunizing a mammal with the peptidyl-resin conjugate.

In still further aspects, the invention concerns an in vitro immunologic-based diagnostic assay that employs peptide-resin conjugates in accordance with the invention. In general, these aspects involve preparing a peptidyl-resin conjugate incorporating a helper T-cell reactive epitope. Next, the peptidyl-resin conjugate is contacted with a body fluid suspected of continuing antibodies capable of binding specifically to the peptide under appropriate immuno-binding conditions. After washing the immunoreacted material in a fashion to remove non-specifically bound antigens or antibodies, as the case may be, the bound antibodies are detected.

The invention may also find use in the construction and/or preparation of vaccines. Thus, important synthetic peptides known to elicit antibodies that prevent infection by a virus could by suitably formatted as a protide and used as a vaccine, e.g., in the vaccination of animals.

BRIEF DESCRIPTION OF THE DRAWINGS

FIG. 5 shows the results of an ELISA comprising rabbit sera after immunization with T-abl-resin and abl-T-resin-conjugates. The results were scored by an ELISA autoreader. Each bar in the figure represents the mean reading of two rabbit antisera of each group.

FIG. 6 shows the result of a protein kinase assay comparing the reactivity of antisera from rabbits immunized with T-abl-resin versus those immunized with abl-T-resin.

DETAILED DESCRIPTION OF THE INVENTION

Figure 2:
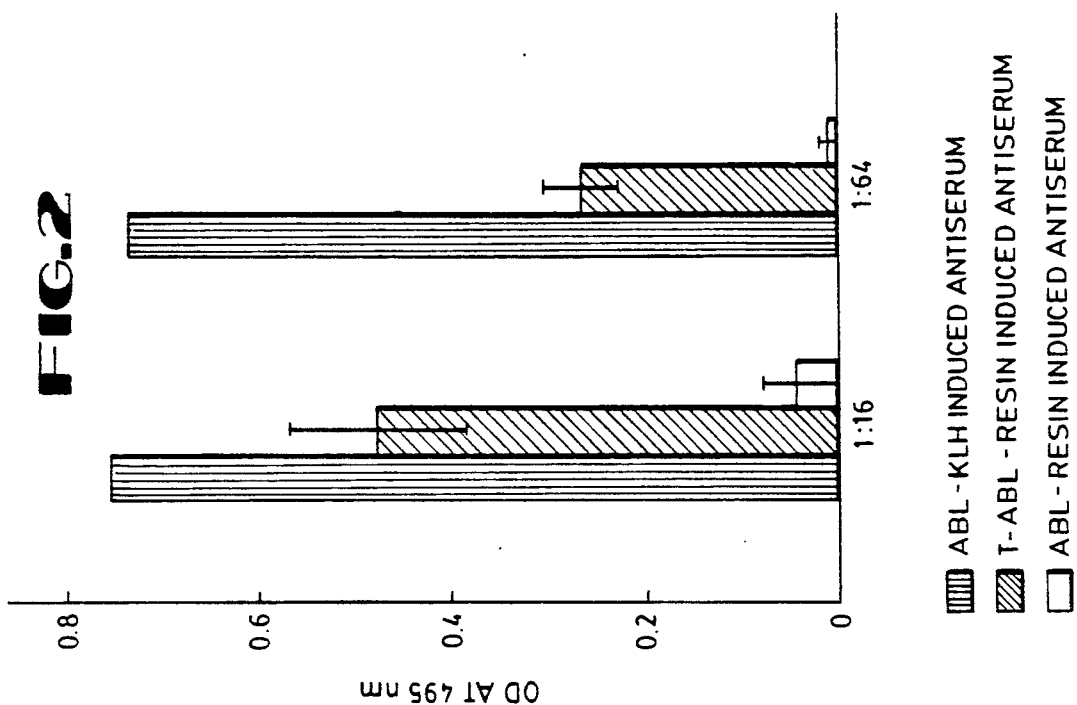
FIG. 2 illustrates a comparative enzyme-linked immunosorbent assay (ELISA) analysis of the peptide antisera produced from rabbits using KLH-abl, T-abl-resin and abl-resin as immunogens. KLH-abl: the peptide was synthesized from the predicted amino acid sequence of Abelson murine leukemia virus abl oncogene (389-403) (11) using solid-phase synthesis (12). Cysteine residues were linked to the carboxyl termini during synthesis for MBS cross-linking through free sulfahydryl groups (13) to the carrier proteins KLH. T-abl-resin: A known T cell epitope of 7 amino acids was synthesized and placed at the NH2-termini of v-abl sequences (389-403) during synthesis and the entire peptide was allowed to remain attached to the resin upon which it was synthesized. abl-resin: The v-abl peptide was synthesized lacking T cell epitope and linked to resin as a control of T-abl-resin. Resin peptides were deprotected with anhydrous hydrogen fluoride under conditions that deprotect the various functional groups on the peptide but allow the bond between the resin and peptide to remain.

The usual method of coupling the selected peptide to polystyrene based resins is through a benzyl ester derivative, and separation of the protide from the resin is usually accomplished by either acidic or basic cleavage. Benzyl esters are susceptible to several such methods of cleavage, but are also stable throughout the multiple deprotection, neutralization and coupling reactions which are characteristic of solid phase synthetic methods. Hydrazine has also been used to separate the protide from the resin (21) as have various ammonolytic (22) and other methods.

However, those methods all require that appropriate steps be taken to avoid damage to the protide followed by purification of the protide from the byproducts of the synthesis, including amino acids, short peptides, decomposition products of the resin, and sometimes, peptides containing incompletely removed protecting groups. Although purification can sometimes be accomplished by a direct crystallization, in syntheses in which the contaminating peptides are of approximately the same size and composition as the desired produce, more selective techniques must be employed. Regardless of the method of separation and purification, those requirements add time-consuming steps to the synthesis which often lower the total yield of protide. The method of the present invention requires no such separation and purification, thereby decreasing the amount of time required to accomplish the synthesis and raising the protide yield.

Polyamide Resin Crosslinking

The polyamide resin of the present invention is prepared by cross-linking a commercially available dimethylacrylamide monomer in aqueous solution using a diaminoalkane, preferably a diaminoalkane having alkenoyl groups at either end of the molecule such as N,N'-bis-alkenoyl-diaminoalkane. In a presently preferred embodiment, the cross-linker is either N,N'-bisacrylyl-1,3-diaminopropane or N,N'-bisacrylyl-1,3-diaminobutane prepared according to the method of Halpern and Sparrow (23), hereby incorporated in its totality by this specific reference thereto. The use of the propane analog is preferred because it yields a polymer of larger pore size and improved swelling properties during protide synthesis than the polymer obtained by use of the ethyl analog. However, it will be understood by those skilled in the art who have the benefit of this disclosure that the other diaminoalkanes listed in that report, N,N'-bisacrylyl-1,2 aminoethane and N,N'-bisacrylyl-1,6-diamino-hexane, as well as other diaminoalkanes, are also appropriate for use in the preparation of the resin of the present invention.

A functional monomer is included in the cross-linked resin of the present invention. The term "functional monomer" refers to those alkenyl amines which are used to anchor the C-terminal amino acid of a synthetic protide to the resin. The functional monomer, when protected with the methylsulfonylethyloxycarbonyl (MSC) group (24), is referred to as an MSC alkenyl amino. Those functional monomers are prepared by reaction of the commercially available chloride derivative with the alkenylamine, and the MSC protective group is subsequently removed with base after polymerization. However, the MSC group is not required. The polyamide resin of the present invention is also prepared by simply adding an excess of the allylamine. The amount of functional monomer added is selected to yield a resin substitution of between about 0.1 mmol and about 0.5 mmol per gram of resin, and preferably in the range of about 0.2 mmol to about 0.4 mmol per gram of resin. The initiator can be any of the initiators known to those skilled in the art such as a persulfate or riboflavin, and is preferably ammonium persulfate.

Because the above-described substances are combined in aqueous solution, they are collectively referred to as "the aqueous phase". The next step in the preparation of the polyamide resin of the present invention is to combine the aqueous phase with an organic phase. The term "organic phase" refers to an organic solvent which, when combined with the aqueous phase and stirred, results in a suspension from which the resin of the present invention is obtained. In a presently preferred embodiment, the organic phase comprises a mixture of hexane and carbon tetrachloride.

An emulsifier is added during the stirring to allow for the formation of beads of uniform size. The emulsifier can be any detergent known to those skilled in the art, and in a presently preferred embodiment, is either sorbitan sesquioleate, sorbitan monolaurate or sorbitan monodecanoate. The amount of detergent added is adjusted to give a spherical resin of approximately uniform size. A decrease in the amount of detergent results in an emulsion which yields increased amounts of larger, amorphous material, which could contribute to a reduction to the internal growing chains of amino acids. An increase in the amount of detergent increases the amount of fine material, which is difficult to remove without the loss of significant amounts of the resin. Those fines clog the reaction vessels of the peptide synthesizer as well as the associated lines and valves.

A promoter is then added to promote the polymerization of the monomers in the suspension, resulting in the formation of beads of the polyamide resin of the present invention. A number of promoters are known to those skilled in the art, but particular success in preparing the polyamide resin of the present invention has been obtained with N,N,N',N',-tetramethylethylenediamine (TEMED). The resulting beads are then filtered and washed, the MSC group (if present) is removed with base, and the beads are dried. The beads may then be sifted through a mesh sieve to insure relatively uniform size. Overall yields using the method of the present invention ranged from about 87% to about 94% from starting monomers.

The aminomethyl, cross-linked polydimethylacrylamide resin of the present invention provides maximum exposure of the protide in an aqueous solution, and the resin-polymer backbone does not restrict the protide conformationally. The exposure of the protide is the result of the ability of the polyamide resin to swell to many times its dry bed volume when highly solvated by water.

Peptide Synthesis Onto The Polyamide Bead

The selected peptides are then synthesized on the beads by coupling to a linker which is attached to the resin with an activator. The term "linker" refers to a linking group which links the carboxyl group of the first amino acid of the protide to the polymeric resin. In the presently preferred embodiment, this linker is an oxylkyl benzoic acid (OBA) to which an amino acid residue is coupled to serve as the first amino acid in the protide chain. Because the OBA linker is used to attach the C-terminal amino acid to the polyamide resin of the present invention, anhydrous hydrogen fluoride can be used to remove the side chain protecting groups from the protide without significant loss of the protide from the resin. In the below-described examples, the amino acid of choice is glycine, which is protected with the t-butyloxycarbonyl (t-Boc) protecting group, but it will be understood by those skilled in the art who have the benefit of this disclosure that the amino acid could be any amino acid, particularly, the amino acid which is the first amino acid in the protide to be synthesized, and that other protecting groups are equally suitable. The glycine residue serves the additional function of a spacer between the protide and the resin-polymer backbone.

The Boc-glycyl-4-(oxymethyl) benzoic acid which is the presently preferred linker was prepared by a modification of the method described by Mitchell, et al. (25). An important modification of the Mitchell, et al. method is the elimination of the use of dimethylformamide as a solvent. That solvent is difficult to evaporate, consequently, even though evaporation can be hastened by raising the temperature, the method is still time-consuming. The activator used to couple the linker to the polyamide resin prepared as described above is diisopropyl carbodiimide and 4-dimethylaminopyridine, but it will be understood by those skilled in the art that other activators such as dicyclohexylcarbodiimide and 4-methylpyrrolindinopyridine are equally suitable for such a purpose.

Helper T-Cell Epitopes

For immunization purposes, helper T-cell epitopes are incorporated into the sequence of the peptidyl portion of the peptide-resin conjugate. This is done so that the protide will provide for both a B-cell and helper T-cell response, an antibody response being mediated by a cognate interaction between hepten-secific B cells and carrier specific helper T cells. To prepare a suitable B cell and helper T cell reactive peptide, a peptide bearing a selected helper T cell epitope is brought into association with a peptide bearing the epitope to be immunologically targeted. While there is no reason why the two epitopes could not be present on separate peptides, e.g., on separate peptides brought into association by cross-linking, disulfide bond formation, or the like. However, one will typically desire to simply select a helper T-cell reactive determinant sequence and incorporate that sequence together with the immunologically targeted sequence into a single peptide or protide sequence.

It has been determined to be particularly advantageous to position the helper T-cell reactive epitope distal of the B-cell reactive epitope of the peptide with respect to the resin. This orientation of epitopes, in contrast to the reverse (i.e., positioning the B-cell epitope distal of the T-cell epitope), will generally provide a significant advantage in terms of enhanced immunogenicity. This orientation can be denoted as follows:

T-B-resin;

with the "T" and "B", respectively, referring to helper T and B-cell reactive epitopes positioned along a peptide extending from the resin.

Generally, the total peptide length will be on the order of about 20 to 50 amino acids. This is because a particular focus of the invention is the site-directed generation of antibodies against immunogenic epitopes, which will generally range from about 10 to about 20 amino acids in length. Additionally, the helper T-cell reactive epitopes will generally range from about 10 to about 30 amino acids in length.

Identification of useful helper T-cell reactive epitopes can be made by reference to techniques known in the art, such as the T-cell proliferation assay described by Milich et al. (20). This assay involves measuring the ability of a peptide to induce primed T-cells in various strains of mice. Mouse strains with varying genotype of major histocompatibility genes are employed to determine the breadth of T-cell response. Briefly, the assay involves injection of peptide into the footpad of the mouse to induce swelling of the popliteal lymph node (behind the knee). Efficient T-helper cell responses are produced by use of 50–100 ug of peptide emulsified in complete Fruends adjuvant. The popliteal node swells noticeably within 10 days. The node is excised, the cells are dispersed, counted, mixed with defined growth medium, and parallel cultures are grown in medium with and without the peptide that was originally injected. T-helper cells primed originally by the peptide in the mouse will respond to added cognate peptide (but not an unrelated sequence) in cell culture by increased cell division. Cell division is measured by $[^3H]$ thymidine incorporation. Another way to measure the priming of T-helper cells is to quantitate IL-2 produced in the culture as a result of cell growth in the presence of the peptide.

A partial listing of reported T-cell epitopes is given in Table I below, along with the particular sequences as well as their designation and publications where they are characterized in more detail. However, the epitopes listed in Table I are illustrative only of preferred embodiments in that it is believed that any such epitope can be employed in the practice of the invention. For additional epitopes one might desire to refer to the scientific literature, such as the review article of Livingstone et al. (28).

TABLE I

| HELPER T-CELL EPITOPES | |
|---|---|
| PROTEIN OR ORIGIN | SEQUENCE |
| Staph. aureus nuclease protein (14) | (a) KMVENAK |
| foot-and-mouth disease virus VP1 protein (15) | (residues 147–160) (b) DLQVLAQKVARTLP(C) |
| Beta galactosidase (16) | T6 peptide (residues 44–52) (c) TDRPSQQLR |
| Malaria parasite circumsporozite (17) | Th2R (residues 326–343) (d) PSDKHIEQYLKKIKNSIS(C) |
| Human immunodeficiency virus gp120 (18) | env T2 (residues 428–4443) (e) KQIINMWQQVGKAMYA |
| Human immunodeficiency virus gp120 (19) | env T2 (residues 112–124) (f) HEDIISLWNQSLK |
| Hepatitis B surface antigen (subtype ayw) (20) | residues 120–132 within the pre-S(2) region (g) MQWNSTTFHQTLQ |

Practical Applications

After synthesis of the peptide on the polyamide resin, the polyamide resin-protide conjugate is used for a number of purposes, including in vitro assays, e.g., conducted by crushing the beaded polyamide resin-protide conjugate with a mortar and a pestle and absorbing the crushed conjugate onto a solid phase such as a microtiter test plate with neutral pH buffer. Serum or other body fluid suspected of containing an antibody capable of specifically binding the protein or peptide on the resin is then incubated with the absorbed conjugate, unbound antibodies are removed by washing, and the bound antibodies are detected by enzyme linked immunosorbent assay, biotin-avidin amplified assay or other detection methods such as are known in the art.

The polyamide resin-protide conjugate can also be used to map antigenic determinants by simply removing a portion of the polyamide resin-protide conjugate at intervals during the synthesis of the protide, deprotecting the protide, and testing each removed portion in serial fashion to determine that point in the synthesis at which the protide binds antibody. This method is made possible by the elimination of the separation and purification steps required in other synthetic methods. The conjugate can also be tested for its ability to bind antibody by crushing and absorbing to a solid support such as a microtiter test plate and assayed as described above. Separation of the protide from the resin and purification of the protide is not required for such an assay.

The polyamide resin-protide conjugate is also useful as an immunogen. The conjugate is used directly for immunization of experimental animals with or without an adjuvant. The term "experimental animal", as used herein, refers to any animal capable of an immune response. The experimental animals of primary interest are mammals, but an immunogenic response can be induced in other experimental animals such as birds using the method of the present invention. For instance, an immune response specific for hepatitis B, as measured by radioimmunoassay, was induced by immunization of rabbits using a conjugate comprised of a synthetic peptide with the same sequence as the hepatitis B antigen (HBsAG) peptide 119-159 emulsified in Freund's complete adjuvant. Similar results, as measured by radioimmunoprecipitation, were obtained with a conjugate comprising a peptide corresponding to the protein coat of the AIDS virus HTLV-III and the polyamide resin of the present invention.

The polyamide resin-protide conjugate would also be valuable as a vaccine reagent. In particular, the T-cell epitope or mixtures of different T-cell epitopes linked to the same B-cell epitope (or mixtures of the B-cell epitopes) derived from the same infections virus (or microbe) could be tailored to optimize the B-cell anti-viral response for a particular species of animal or similarly for use in man.

EXAMPLE I

Preparation of Functional Monomer

Five grams of (26.8 mmol) 2-methylsulfonyl ethyloxycarbonyl chloride (MSC chloride) (K + K Labs, ICN) were dissolved in 15 ml acetonitrile and added dropwise over a 20 minute period to a stirred solution of 2.1 ml (28 mmol) redistilled allylamine (Kodak) and 4.9 ml (28 mmol) redistilled diisopropylethylamine (DIEA) in 20 ml acetonitrile. (DIEA (Aldrich) was refluxed over ninhydrin and redistilled.) The solution was stirred an additional tow hours and the solvent evaporated. The residue was taken up in 250 ml ethyl acetate and allowed to stand for one-two hours. The bulk of the DIEA hydrochloride salt precipitated as needles. After filtration and evaporation, the crude material was dissolved in a minimal amount of chloroform and loaded onto a silica gel G-60 column (60 g) packed in he same solvent. Elution with chloroform yielded pure MSC-allylamine. ($R_F$ on TLC—0.64 (Solvent—CNCl$_3$: CH$_3$OH, 9:1).)

The remaining DIEA salts adsorbed to the column under these conditions. Occasionally, material migrating near the solvent front on TLC contaminated the MSC-allylamine column fractions. That material was removed by crystallizing the MSC allylamine from methylene chloride-hexane at −20° C. Yield was 4.8 g (85% from MSC chloride).

EXAMPLE II

Preparation of Cross-Linker

The cross-linker N,N'-bisacrylyl-1,3-diaminopropane was prepared according to the method set out in Helpern and Sparrow, supra. Briefly, diaminopropane (Aldrich) was dissolved in acetonitrile and added dropwise to an acrylyl chloride-acetonitrtile solution at 4° C., allowed to warm to room temperature and stirred. The diaiminopropane dihydrochloride was removed by filtration, washed with warm acetonitrile, and the combined filtrates were concentrated in vacuo. N,N'-bisacrylyl-1,3-diaminopropane was crystallized at 4° C. overnight and the resulting plates filtered and dried in vacuo.

EXAMPLE III

Preparation of Polyamide Resin

In a glass, 2-liter cylindrical, fluted polymerization vessel fitted with a nitrogen inlet and mechanically driven glass stirrer were added 490 ml hexane and 290 ml carbon tetrachloride. The solution was purged for 15 minutes with nitrogen to remove oxygen. To this solution was added an aqueous solution containing N,N'-bisacrylyl-1,3-diaminopropane (2.9 grams, 15.9 mmol) prepared as described in Example II mixed with 18.2 ml (175 mmol) of N,N-dimethylacrylamide (PolySciences). Ten g (48 mmol) MSC allylamine prepared as described in Example I and 120 ml water were added, and the solution was filtered and degassed before addition to the organic phase. The density of the resulting mixture was adjusted to obtain a uniform suspension with stirring at 400-450 RPM. Ammonium persulfate (BioRad) (0.5 g in 5 ml H$_2$O) and 1 ml of either sorbitan sesquioleate or sorbitan monolaurate (Sigma) were added.

A solution of 3 ml N,N,N',N,-tetramethylethylenediamine (TEMED) (BioRad) in 2 ml H$_2$O, pH 6.5-7.5 (conc. HCl) was then added to the suspension. The suspended emulsion was stirred for two hours under nitrogen atmosphere. The resultant beaded material was then filtered and washed sequentially with water (one liter) methanol (one liter), a mixture of dioxane:methanol:2N NaOH (14:5:1, two liters, to remove MSC group), water (two liters), 1N HCl (two liters), water (two liters), and then methanol (two liters). The resin was defined by suspension in methanol and decanting (3×). After swelling in methylene chloride (Baker HPLC grade), the resin was shrunk in hexane and dried in vacuo. Large amorphous material was removed by sifting the resin through an 80 mesh (180 micron) sieve.

The degree of functionalization was checked by coupling Bocalanine to 100 mg of the resin using diisopropylcarbodiimide as activator and 4-dimethylaminopyridine (recrystallized from ethyl acetate) as catalyst. Amino acid analysis showed a substitution of 0.15 to 0.35 mmol/g resin, depending on the lot, and resins were prepared with as little as about 0.1 and as much as about 0.5 mmol/g resin depending upon the amount of allylamine added. The loaded resin gave no detectable staining with picryl-sulfonic acid, indicating the absence of unreacted free amino. When swollen in methylene chloride, the beads occupied about 2.5 times their dry bed volume. When swollen in dimethylformamide or an aqueous solution, the beads occupied approximately fur and six times their dry bed volume, respectively.

EXAMPLE IV

Preparation of Linker

The linker Boc-glycyl-4-(oxymethyl) benzoic acid was prepared by modification of the method of Mitchell et al., supra. Briefly, the 4-(bromomethyl) benzoic acid phenylacylester was prepared by dissolving 10.3 ml redistilled diisopropylethylamine and 12.5 g (60.6 mmol) bromoacetophenone in 450 ml ethyl acetate. 4-(bromomethyl) benzoic acid (13.89 g, 60.6 mmol) was added in seven equal portions over a three hour period to the stirred solution at 40-50° C. Stirring was continued for two more hours at room temperature. Precipitated Et$_3$N HBr was removed by filtration and the ethyl acetate solution was washed four times with 50 ml each of an aqueous solution of 10% citric acid, saturated sodium chloride, saturated sodium bicarbonate, and saturated sodium chloride. The organic phase was dried over anhydrous magnesium sulfate and freed of solvent by rotary evaporation under reduced pressure. The residue was crystallized from CH$_2$Cl$_2$-petroleum ether (1:3 v/v) to give the 4-(bromomethyl) benzoic acid phenylacylester.

The 4-(bromomethyl) benzoic acid phenylacylester was converted to Boc-glycyl-4-(oxymethyl) benzoic acid by dissolving Boc-L-glycine (25 mmol, 4.38g) in 15 ml methanol and titrating to neutrality with tetramethylammonium hydroxide (25% in methanol). Solvent was removed azeotropically with chloroform in vacuo, and the salt dissolved in 150 ml acetonitrile. To the stirred solution was added 5.8 g (17.5 mmol) of the 4-(bromomethyl) benzoic acid phenacyl ester prepared as described. After overnight mixing, the precipitated tetramethylammonium bromide was filtered and the solvent evaporated. The residue was dissolved in 400 ml ethyl acetate and the solution filtered.

The organic phase was then washed successively with 10% aqueous citric acid (3×75 ml), 0.5M sodium bicarbonate; 0.5M potassium carbonate (2:1), pH 9.5 (8×75 ml), then water (3×75 ml). The solution was dried (MgSo$_4$) and the solvent removed in vacuo. The residue was dissolved in 200 ml of 85% acetic acid to which 23 g acid washed zinc dust was added. The mixture was stirred until the phenacyl ester was no longer visible by TLC (4-5 hours). The zinc was filtered and washed with 50 ml acetic acid, and the combined solutions were lyophilized. The residue was suspended in 100 ml water:300 ml ethyl acetate, and the pH adjusted to 1.5 (conc. HCl). The aqueous layer was extracted with a second portion of ethyl acetate (200 ml), and the combined extracts were washed with water (100 ml). After drying (MgSO$_4$) and evaporating, the Boc-glycyl-4(oxymethyl) benzoic acid was purified by recrystallization from methylene chloride:hexane at −10° C. Yield was 4.5 g (14.5 mmol, 83% from the phenacyl ester).

EXAMPLE V

Coupling of Linker to Polyamide Resin

Boc-glycyl-4-(oxymethyl) benzoic acid prepared as described in Example IV was coupled to the aminomethyl polyamide resin (1.2 g) prepared as described in Example III on a Biosearch Sam II automated peptide synthesizer using diisopropylcarbodiimide and dimethylaminopyridine as activator in a 1:1 methylene chloride:dimethylformamide solution. Both methylene chloride (Baker HPLC grade) and dimethylformamide (Baker Photrex grade) were used without further purification. Following treatment with hydrogen fluoride, 50 mg of the glycyl resin was found to contain 0.13 mmol/g by amino acid analysis. Amino acid analysis was performed using a Beckman Model 119 amino acid analyzer following either a two hour hydrolysis (12N HCl:propionic acid, 1:1, 135° C.) or 24 hour hydrolysis (6N HCl, 110° C.) of resin bound peptides.

EXAMPLE VI

Synthesis of Hepatitis B Antigen Peptide

The hepatitis B surface antigen (HBsAg) peptide 119-159 was assembled on the aminomethyl, cross-linked polydimethylacrylamide resin prepared as described in Example III, having the Boc-glycyl-4-(oxymethyl) benzoic acid linker prepared as described in Example IV attached thereto using the method described in Example V, with all residues being double coupled using a Biosearch Sam II automated peptide synthesizer. The sequence of that HBsAg peptide is as follows, and is relative to the AYW subtype:

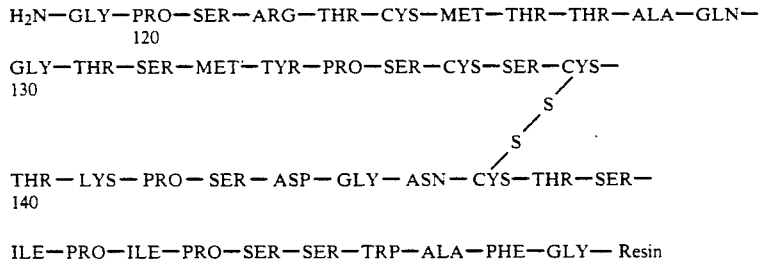

The peptide included the following substitutions to control the specific formation of disulfide loops: serline for cysteines 121, 138, and 149. The cysteines 139 and 147 sulfhydryls were blocked by the 4-methoxybenzyl group, while the sulfhydryls of cysteines at 124 and 137 were protected as the S-acetamidomethyl derivatives. Alpha-N-tBoc protected amino acids were purchased from Bachem. Additional side chain protecting groups were as follows: formyl group for the indole nitrogen of tryptophan; benzylethers for threonine and serine hydroxyls; acetamidomethyl or 4-methoxybenzyl for cysteine sulfhydryls as described above; benzyl esters for betacarboxyl of aspartic acid and the gamma-carboxyl of glutamic acids; 2-chlorobenzyloxycarbonyl for E-amino group of lysine; 2,6-dichlorobenzyl ether for the phenolic hydroxyl of tyrosine; and the p-tosyl group for the quanidine of arginine. For the synthesis, methylene chloride (Baker HPLC grade) and DMF (Baker Photrex grade) were used without further purification. Diisopropylethylamine (DIEA) (Aldrich) was refluxed over ninhydrin and redistilled. Trifluoroacetic acid (Halocarbon) was redistilled, with the middle cut used in deblocking steps. All other chemicals were reagent grade or better and used without further purification.

Side chain protecting groups were removed from the completed peptidyl-resin by treatment with anhydrous HF (20 ml/g resin) at 0° for thirty minutes, containing 10% anisole and 2% ethanedithiol. Following evaporation of HF, the peptidyl-resin was washed successively with ether, 1% acetic acid, methanol, 5% DIEA in methylene chloride, methanol, then 1% acetic acid. The peptidyl-resin was dried in vacuo. The formyl group was removed from the tryptophan by treatment with ethanolamine at 0°. A disulfide bridge was formed between cysteines 139 and 147 by potassium ferricyanide treatment. A second disulfide bridge between cysteines 124 and 137 resulted during simultaneous removal of the acetimidomethyl moieties with a solution of iodine in acetic acid.

EXAMPLE VII

In Vitro Assay For Presence of HBsAg Antibody

Human serum can be assayed for the presence of antibody specific for the HBsAg peptide 119-159 by the following in vitro assay. A quantity of the HBsAg peptide 119-159-polyamide resin prepared as described in Example VI is crushed with a mortar and pestle. A microscope may be used to verify that the polyamide resin-peptide conjugate has been crushed. Approximately 100 ul of a solution containing between about 200 nanograms and about 10 micrograms of the crushed polyamide resin-peptide conjugate in a neutral pH buffer such as phosphate buffered saline (PBS) is absorbed to a solid phase such as Dynatech Immunolon II Microfilter test plate. Nonspecific binding sites are blocked with 10% normal goat serum (NGtS) and the plate is washed with Tween 20 PBS (T-PBS) to remove unbound antibodies.

Human sera suspected of containing antibodies specific for HBsAg peptide 119-159 and rabbit antisera produced by immunizing rabbits with this polyamide resin-HBsAg peptide 119-159 conjugate diluted in 10% NGtS is then added to the polyamide resin-peptide-coated plate and incubated for one hour at 37° C., followed by washing with T-PBS. Biotin goat anti-human IgG or biotin goat anti-rabbit IgG (Vector Laboratories, Burlingame, Calif.) is then incubated with the bound human and rabbit sera, respectively, for one hour at 37° C. The wells are washed and avidin conjugated to horseradish peroxidase (Av-HRP) is added for 20 minutes at room temperature. The wells are then washed with T-PBS to remove an unbound Av-HRP and peroxidase activity is determined using a 1 mN solution of 1,2'-azino-di(3-ethyl-benz-thiasoline sulfonic acid) Sigma Chemical Co.) and 0.03% $H_2O_2$ as substrate. The reaction is stopped with 5% (w/v) sodium dodecyl sulfate in water prior to quantitating spectrophotometrically at 10 nm using a Dynatech plate reader. Optimal dilutions of each reagent are selected by titration.

EXAMPLE VIII

In Vitro Assay for Presence of HBsAg Antibody

Human serum was assayed for the presence of antibody to hepatitis B surface antigen by the following in vitro assay. A 10% solution of the polyamide resin-HBsAg peptide 119-159 conjugate was prepared in a buffered bovine serum albumin (BSA) solution containing a final concentration of 40% tetrahydrofuran. An equal volume of antibody specific for the HBsAg peptide 119-159 containing between 100,000 and 1,000,000 counts per minute $I^{125}$ was added and incubated with gentle rocking. The resulting suspension was centrifuged and the pellet washed with 1% BSA-Tween 20 PBS, then centrifuged again. The radioactivity of the pellet was then counted in a Gamma counter. The results clearly indicate the recognition of the polyamide resin HBsAg peptide 119-159 conjugate by native HBsAg antibody:

|  | Glycyl resin (Control | HBsAG peptide 119-159 conjugate |
|---|---|---|
| IgG Human anti-HB#1 | 1240 cpm* | 22,840 |
| IgG Human anti-HB#2 | 1921 | 28,732 |
| Normal human IgG | 1432 | 1949 |

*all measurements in counts per minute

EXAMPLE IX

Use of Polyamide Resin-Protide Conjugate to Induce an Immunogenic Response in Mammals The polyamide resin-peptide conjugate prepared as described in example VI was used to induce an immunogenic response tin rabbits as follows. New Zealand white female rabbits were immunized with three monthly intramuscular injections of either 200 ug HBsAg peptide 119-159 (as the peptide-resin conjugate) or only glycyl-resin emulsified in Freund's complete adjuvant (range of immunogen, 50 ug to 1 mg for rabbits). Serum was collected after bi-weekly bleeding and checked for anti-HBsAg activity using a commercially available radioimmunoassay (RIA) kit (AUSAB, Abbott Laboratories). The recognition of the native HBsAg surface antigen by the anti-peptide 119-159 antibody response induced in the rabbits is demonstrated by the following data developed by that RIA.

| RABBIT | IMMUNOGEN | IMMUNIZATION | ANTIBODY TITER[a] (RIA UNITS PER MILLILITER) |
|---|---|---|---|
| No. 1 | Glycine-Resin | Preimmune[a] | —8[b] |
|  |  | Primary | —8 |
|  |  | Secondary | —8 |
|  |  | Tertiary | —8 |
| No. 2 | HBsAg Peptide-Resin | Preimmune | —8 |
|  |  | Primary | —8 |
|  |  | Secondary | 183 |
|  |  | Tertiary | 920 |
| No. 3 | HBsAg Peptide-Resin | Preimmune | —8 |
|  |  | Primary | —8 |
|  |  | Secondary | 72 |
|  |  | Tertiary | 262 |

[a]Sera obtained prior to immunization.
[b]Antibody titer to HBsAg is below the sensitivity of the RIA kit and is considered not to contain specific antibodies.

As can be seen by this data, the polyamide resin-HBsAg peptide 119-159 conjugate containing a single disulfide bridge between cysteines 139 and 147, when used to immunize rabbits, yielded anti-peptide antisera which cross reacted with HBsAg.

EXAMPLE X

Synthesis of HTLV-III Antigen Peptide

The HTLV-III peptide gp 120 503-532 was assembled on the cross-linked polydimethylacrylamide resin prepared as described in Example III, having the Boc-glycyl-4-(oxymethyl) benzoic acid linker prepared as described in Example IV attached thereto using the method as described in Example V, in he same method as described for the synthesis of the HBsAG peptide 119-159 in Example VI, the only difference being the order in which the protected amino acids were added. The sequence of the HTLV-III peptide gp 120 503-532 is as follows:

H$_2$N—VAL—ALA—PRO—THR—LYS—ALA—LYS—ARG—ARG—
503
VAL—VAL—GLN—ARG—GLU—LYS—ARG—ALA—VAL—GLY—
ILE—GLY—ALA—LEU—PHE—LEU—GLY—PHE—LEU—

GLY—ALA—GLY—O—CH$_2$— 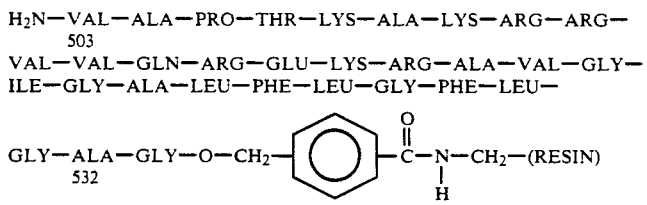
532

EXAMPLE XI

Figure 1:
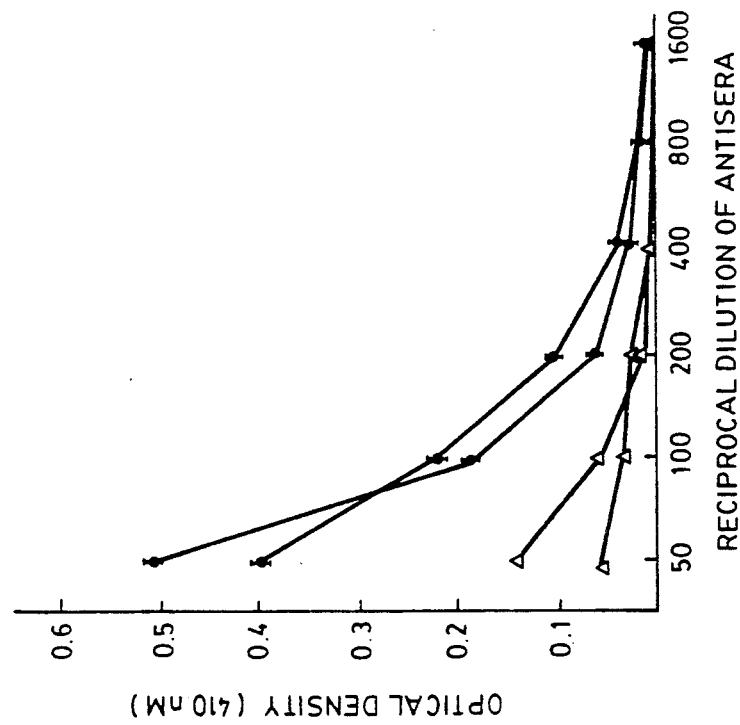
FIG. 1 is a graph of optical density at 410 nm as a function of the reciprocal dilution of rabbit antisera to the polyamide resin-NTLV-III peptide 503-532 conjugate obtained by enzyme linked immunosorbent assay. The circles represent data from rabbits immunized with that conjugate, the triangles represent data from those some rabbits before immunization.

Use of Polyamide Resin-HTLV-III Synthetic Peptide Conjugate to Induce an Immunogenic Response Rabbits immunized with the polyamide resin-HTLV-III peptide 503-532 conjugate produced a specific anti-peptide response as determined by an enzyme linked immunosorbent assay conducted according to the method of Example VII (with the use of antisera produced by immunizing the rabbits with the polyamide resin-HTLV-III peptide 503-532 conjugate rather than the conjugate which included the HBsAg peptide 119-159 as used in that Example). The results of that immunoassay are presented graphically in FIG. 1. The data represented by the circles is data from rabbits immunized with that conjugate, the data represented by triangles is from those some rabbits before immunization (the solid circles and triangles are both from one rabbit; the open circles and triangles are both from one rabbit; the open circles and triangles are both from a second rabbit). A conjugate comprised of the polyamide resin and a third peptide failed to demonstrate significant binding. One of the rabbits produced an anti-HTLV-III response specific for the gp 120 envelope protein of HTLV-III based on a radioimmunoprecipitation assay conducted according to the method of Allan, J. S., et al. 228 Science 1091 (1985) and Barin, F., et al., 228 Science 1094 (1985), both of which are incorporated herein in their entirety by this specific reference thereto.

The ability of the rabbit antisera generated to peptide 503-532 to neutralize HTLV-III infectivity was assessed on the basis of a reduction of reverse transcriptase activity using a tenfold dilution of the HTLV-III stock with a constant amount of antisera. Barre-Sinoussi, F., et al., 220 Science 868 (1983). A single rabbit anti-peptide 503-532 antiserum efficiently reduced HTLV-III replication at day 20 compared to pooled human sera from AIDS patients at tenfold dilutions of virus. A second rabbit antiserum to that peptide failed to reduce HTLV-III replication and so was used as a control throughout the RT assay. No anti-HTLV-III activity was detected in this particular antiserum based on radioimmunoprecipitation even though the rabbit received a similar immunogen and produced a detectable anti-peptide response.

The antiserum that neutralized HTLV-III detected both gp 120 and gp 160 envelope glycoproteins. This rabbit antiserum was found to be less efficient in neutralizing HTLV-III compared to human AIDS serum on day 12 and 15 following HTLV-III infection.

EXAMPLE XII

Augmentation of Site-Directed Antibody Production by a Synthetic T-Cell Epitope Presented as a Resin Peptide Conjugate A carrier protein cross-linked synthetic peptide predicted from the v-abl oncogene sequence (residues 389-403) efficiently stimulated the production of IgG antibodies. These antibodies were found to bind and immunoprecipitate the native protein encoded by the gag-abl genes of Abelson murine leukemia virus. The antibodies also bound the product of fused bcr-abl genes present in leukemic cells from Philadelphia chromosome-positive human chronic myelogenous leukemia patients. In the exemplary studies described below, it was found that the v-abl peptide when linked to a T-cell active peptide as a continuous peptide and while still attached to the resin on which it was synthesized, stimulated the production of IgG antibodies that bound and immunoprecipitated $P210^{bcr-abl}$. The v-abl peptide-resin complex lacking the T-cell epitope was very inefficient in this type of activity.

A synthetic peptide predicted from the Abelson murine virus abl oncogene [residues 389-403, DEVEKELGKRGTRGG-C (11)] was synthesized with a T-cell active epitope of 7 amino acids [KMVENAK] placed at its N-terminus (T-abl-resin). The peptide blocking groups were removed under conditions that leave the entire peptide linked to the polyamide resin upon which it was synthesized (12). The v-abl peptide, lacking the T-cell active peptide termed (abl-resin), was also synthesized in the same manner. As a control the v-abl peptide was released from the resin and chemically cross-linked to Keyhole limpet hemocyanin (KLH) (13). Each preparation was suitably adjuvanted and inoculated into NZW rabbits and serum taken at various times to measure the titer of anti-peptide antibody.

T-abl-resin and abl-resin preparation were grounded in a tight-fit homogenizer with 20 strokes before use. Each preparation (500 ug) was suspended in 1.5 ml of PBS and emulsified with another 1.5 ml of complete Freund's adjuvant. The rabbits were injected subcutaneously at multiple sites. There were three rabbits for T-abl-resin and three rabbits for the abl-resin but only one rabbit for KLH-abl. Two booster injections of each preparation in incomplete Freund's adjuvant were given at 2-week intervals. The rabbits were bled 2 weeks after the last booster and the titer of antisera against v-abl peptide were assayed by ELISA compared to pre-immune sera. For peptide-based ELISA, 50 ng of v-abl peptide in 0.1M NaHC03, pH 9, were plated in wells of 96-well plate and dried overnight at 37° C.

Next day, the remaining sites in each well were blocked by a TN solution of 50 mM Tris-HCL, pH 7.6, and 50 mM NaCL with 5% nonfat dry milk (Food Club) for 1 hour at 37° C. The plate was washed 6 times with TN solution with 0.5% Tween 20 (Sigma). Fifty ul of peroxidase conjugated goat anti-rabbit IgG (1:4000) (Boehringer Mannheim Biochemicals) in TN buffer with 5% nonfat dry milk were added to each well.

After incubating for another hour at 37° C. the plate was washed 6 times with above TN solution. The substrate used was 0-phenylene-diamine (OPD) (Sigma). Fifty ul of substrate solution were added to each well and incubated for 20 mins at room temperature before the plate was read with a ELISA autoreader at 495 nm. The ELISA OD reading in the figure was presented as net. In order to compare each group, the OD reading was presented as net value (subtracted the pre-immune from immune sera) and as average of 3 rabbits in each group with standard deviation.

The sera were screened for IgG and IgM antibodies in an ELISA using the v-abl peptide as the antigen (FIG. 2). The T-abl-resin greatly stimulated the immune response giving significantly higher anti-abl peptide titers than the abl-resin peptide complex. The sera were found to have predominantly IgG molecules with only trace levels of IgM (data not shown) and the titer increased dramatically around 2 weeks after the second booster shot (data not shown). The v-abl peptide inoculated as a cross-linked peptide (abl-KLH) produced the highest antibody response in rabbits as compared to the resin-bound peptides (FIG. 2).

The T-cell epitope employed in this study was derived from Staph. aur. nuclease (14). Given the wide spread occurrence of this bacterial organism, it was of interest to determine whether rabbits have been primed with this particular antigen. Pre-bleeds were found to contain significant but variable titers of IgG antibody that bind to Staph. aur. nuclease protein in ELISA tests. After immunization with all three antigen preparations, the titer of antibody to Staph. aur. nuclease antigen was variable stimulated.

The value of an anti-peptide antibody lies in its ability to recognize the native protein encoded by the gene sequence from which the immunogenic peptide was derived. Experiments were therefore performed to determine whether or not the anti-peptide sera generated from the T-abl-resin would recognize an authentic abl gene product. For this purpose, the 210,000 molecular weight protein ($P210^{bcr-abl}$), produced by the fused bcr and abl genes present in cell lines derived from Philadelphia chromosome-positive chronic myelogenous leukemia patients was chosen. Studies had shown that hyperimmune rabbit sera prepared against the v-abl (389-403) peptide efficiently detects gag-abl and bcr-abl proteins in cell extracts by immunoprecipitation (21).

These experiments involved in part, the performing of in vitro immune complex kinease assays of P210 bcr-abl protein from a ph positive CML cell line, K562. In these assays K562 cells ($10^7$ per lane) were disrupted in 1 ml of lysis buffer (0.1% Triton X-100, 5 mM EDTA. 100 mM NaCL, 100 KIU $ml^1$ Trasylol in 10 mM sodium phosphate, pH 7.2) with 10 strokes in a tight-fitting homogenizer. Lysates were subjected to 100,000 g centrifugation for 1 hour at 4° C. and the supernatants were harvested to react with antisera for 1 hour on ice. The immune complexes were then precipitated by incubation with 20 ul of 50% Protein A-sepharose in PBS for 15 min on ice. The immunoprecipitates were washed once with RIPA buffer (0.1% Triton X-100, 0.05% SDS, 5 mM EDTA, 100 mM NaCL in 10 mM sodium phosphate, pH 7.2), wash buffer (0.1% Triton X-100, 100 mM NaCL in 10 mM sodium phosphate, pH 7.2), and 50 mM Tris-HCL, pH 7.5, respectively.

Figure 3:
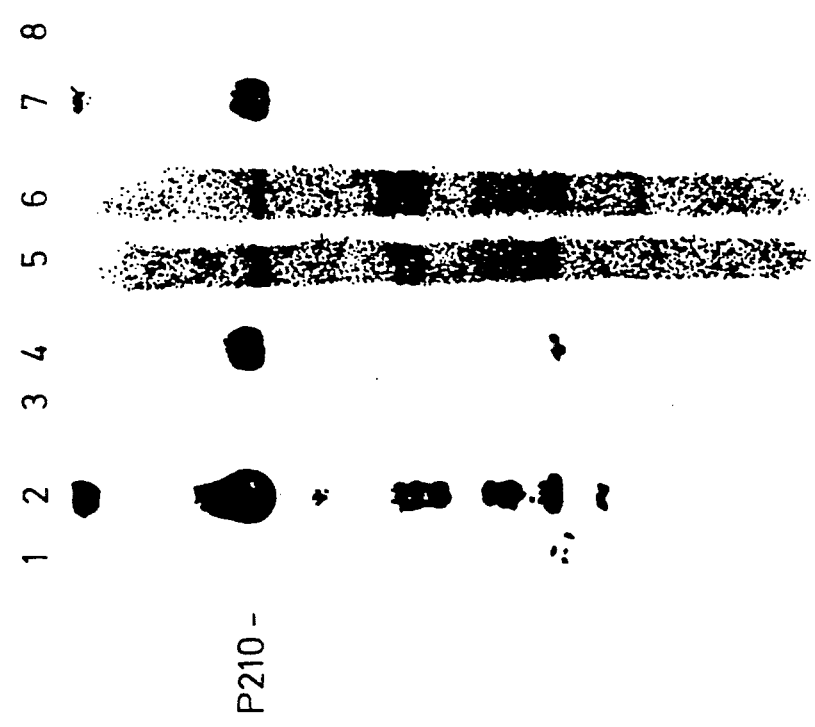
FIG. 3 shows the result of in vitro immune complex kinase assays of P210 bcr-abl protein from ph positive CML cell line (K562). Antisera 20 ul used were anti-abl 389-403 produced from rabbits using KLH-abl (lane 2), T-abl-resin (lane 4 and abl-resin (lane 6) as immunogens. In odd lanes (1,3,5), the preimmune sera (20 ul) of respective rabbits were used as control Lane 7, 20 ul of antiserum from T-abl-resin rabbit was used and the reactivity of this antiserum was blocked by addition of its cognate peptide (5 ug) (lane 8).

The pellets were resuspended in 50 ul of 20 mM Hepes, pH 7.0, containing 0.1% Triton X-100, 100 mM NaCL, and 10 mM MnCL2. The kinase assay was initiated with addition of 10 Ci [$^{32}$P]0 ATP (3000 $mmol^{-1}$) and incubated for 10 min on ice. The reaction was stopped by addition of RIPA buffer and the immune complex was washed once with RIPA buffer and then prepared for electrophoresis on 6% SDS-PAGE (22). The phosphorylated proteins were sized with pre-stained markers. The gel was exposed 30 min on Kodak XRP-1 film. As FIG. 3 shows, the antibody produced from the T-abl-resin-peptide containing the T-cell epitope efficiently detected $P210^{bcr-abl}$ as measured by an immune complex protein kinase assay (FIG. 3, lane 4). This assay involved immunoprecipitation of P210 and incubation of the immune complex with [$^P$] ATP. The specificity of this reaction was demonstrated in a competition experiment in which the anti-peptide antibody was pre-treated with excess synthetic peptide to render the anti-peptide antibody incapable of recognizing P210 (FIG. 3, lane 8). The antibody raised against the abl-resin peptide lacking the T-cell epitope had only a very weak ability to detect $P210^{bcr-abl}$ (FIG. 3, lane 6).

Figure 4:
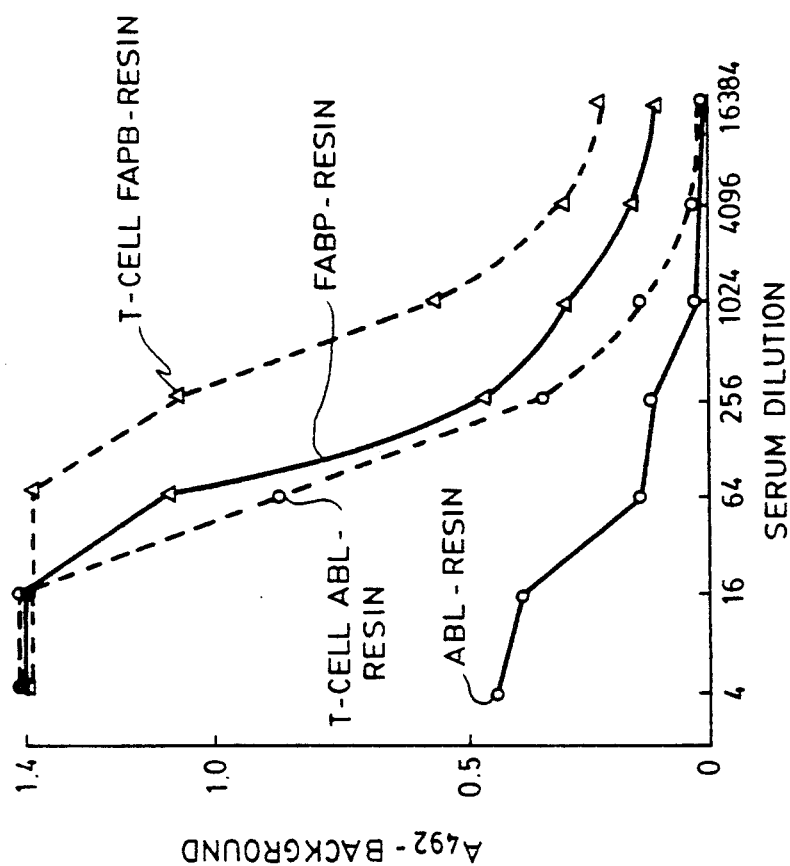
FIG. 4 shows the results of an ELISA comparing rabbit sera after 3 injections of four synthetic peptide hydrophilic resin conjugates. A dramatic enhancement (5-50 fold) of the immune response is seen from the two peptides containing the T-cell epitope of Staph. A nuclease, T-abl-resin and FABP-resin (fatty acid binding protein).

Depicted in FIG. 4 are the results of ELISA of rabbit sera after three injections of four synthetic peptides, including abl-resin, T-cell-abl-resin, fabp-resin (fatty acid binding protein) and T-cell-fabp-resin. As can be seen, there is a dramatic enhancement (5-50 fold) of the immune response from both peptides incorporating the T-cell epitope of Steph. A nuclease.

These data provide important new insights into the role of primary protein sequences in the generation of useful humoral immune response to a specific antigen. The results raise the real possibility that generic T-cell specific epitopes exist in defined synthetic peptides, and that these generic T-cell sites can be used to provide T-cell help for antibody production to variety antigenic sites in proteins capable of binding a specific antibody. Moreover, the preparation of antibodies of predetermined specificity has taken another quantum jump since the carrier protein can now be eliminated from the routine steps required to produce useful antibody from either synthetic peptides or short fragments of proteins.

This new data has positive implications for generating defined reagents for the purpose of developing useful diagnostic tests and vaccines.

EXAMPLE XIII

Production of Rabbit Antisera Against v-abl (389-403)

1. Reagent: abl-KLH; T-cell-abl-resin; abl-resin
2. Booster: once every two weeks, 4 times in total
   500 ug of v-abl peptide
   3 mg of T-cell-abl-resin (about 500 ug of v-abl peptide)
   3 mg of abl-resin (about 500 ug of v-abl peptide
3. ELISA titers assayed 20 day after 3rd and 4th booster serum:

|   | Dilution | abl-KLH | T-abl-resin | abl-resin |
|---|----------|---------|-------------|-----------|
| A | 1:64     | —       | 0.87#       | 0.132     |
|   | 1:256    | —       | 0.344       | 0.11      |
| B | 1:64     | over 1.5| 1.162       | 0.353     |
|   | 1:256    | over 1.5| 0.448       | 0.095     |

A: 10 days after the 3rd booster
B: 10 days after the 4th booster
ELISA reading at OD 495 nm.
4. PK Assay 10 Days After The 3rd Booster:
   abl-KLH (5 ul): +++
   T-cell abl resin (20 ul): ++++
   abl-resin (20 ul): ±
   KLH standard (5ul): ++++

EXAMPLE XIV

Comparison of Immunogenicity of Resin-Peptide Conjugates: T-ABL Resin Versus ABL-T-Resin Four rabbits were divided into two groups (2 rabbits/group) and one group was immunized with T-abl-resin while the other group was immunized with abl-T-resin. After four booster injections, rabbits were bled and antisera from each analyzed by ELISA and protein kinase assays, run essentially as described in Example XIII. The respective peptides were prepared by synthesis of the v-abl peptide and *Staph. aureus* T-cell epitope directly onto a polyamide resin essentially as described above.

The ELISAs were performed so as to detect the relative degree of specific immunoresponse to the v-abl peptide (KENLLAGPSENDPN[C]) in the rabbits immunized respectively with T-abl-resin and abl-T-resin conjugates. Briefly, 50 ng of v-abl were coated on each well of a 96-well ELISA plate. Rabbit antisera, diluted 1:16 and 1:64, were reacted with the peptide. The results are displayed graphically in FIG. 5.

As can be seen in FIG. 5, the T-abl-resin configuration elicited an approximately 2- to 4-fold greater immune response directed against the v-abl peptide as compared to the abl-T-resin configuration, depending on antisera dilution.

The rabbit sera were also tested in a protein kinase assay essentially as described above in Example XIII. The results are shown in FIG. 6. Rabbit 7L087 (lane 1-3) was immunized with T-abl-resin and rabbits 7L112 (lane 4-6) and 7L113 (lane 7-9) represent the abl-T-resin group. Lanes 1, 4, and 7 are pre-immune sera. Lanes 2, 5, and 8 are antisera pre-blocked with excess v-abl peptide. Lanes 3, 6, and 9 were antisera without pre-blocking. As can be seen from FIG. 6, the T-abl-resin construct produced a significantly higher specific response (lane 3) than the abl-T-resin construct (lanes 6 and 9). In 7L113, the signal was quite faint (lane 5 and 6), and in the other abl-T-resin immunized rabbit, 7L112, the response was not much greater. In neither case did the antisera contain specific antibody to the native protein p210. However, rabbit 7L087, one of the T-abl-resin immunized rabbits, exhibits a strong response (lane 3). A similarly strong response was seen in the other rabbit receiving T-abl-resin, rabbit 7L086 (results not shown).

In further studies employing ELISAs designed to measure the anti-*S. aureus*-T-cell epitope response in rabbit sera demonstrated that such anti-T-cell epitopes could be detected. This indicated that some B-cell response will also be realized against the T-cell epitope.

The foregoing examples are presented for purposes of exemplification of the method of the present invention. Variations in those methods will be known to those skilled in the art, and it is expected that all such variations will be made without departing from the spirit and scope of the present invention as claimed in the following claims.

REFERENCES

The references listed below are incorporated herein by reference to the extent that they supplement, explain, provide a background for or teach methodology, techniques and/or compositions employed herein.

1. Merrifield, R. B. (1969), "Solid-phase Peptide Synthetic", *Adv. Enzymology*, 32:221.
2. Atherton et al. (1975), *J. Amer. Chem. Soc.*, 97:6584.
3. Arshady et al. (1979), "Easily Prepared Polar Support For Solid Phase Peptide And Oligonucleotide Synthesis", *J. C. S. Chem. Comm.*, 425.
4. Dreesman et al. (1982), *Nature*, 295:158.
5. Lerner et al. (1981), *Proc. Natl. Acad. Sci. USA*, 78:3403.
6. Prince et al. (1982), *Proc. Natl. Acad. Sci. USA*, 79:579.
7. Sanchez et al. (1982), *Intervirology*, 18:209.
8. Kennedy et al. (1987), *Jrnl. Biol. Chem.*, 262:5769.
9. PCT Application Publication Number WO 87/06594, published 11/5/87.
10. Chanh et al. (1986), *EMBO Jrnl.*, 5:3065.
11. Reddy et al. (1983a), *Proc. Natl. Acad. Sci. USA*, 80:3617; Reddy et al. (1983b), *Proc. Natl. Acad. Sci. USA*, 80:7372.
12. Sparrow, J. T. (1976), *J. Organ. Chem.*, 41:1350.
13. Liu et al. (1979), *Biochemistry*, 79:690.
14. Van Regenmortel *Annals Inst. Pasteur*, 137E:497 (1986).
15. Francis et al. (1987), *Immunology*, 61:1.
16. Krzych et al. (19880), *FASEB J.*, 2:141.
17. Good et al. (1987), *Science*, 235:1059.
18. Cease et al. (1987), *PNAS*, 84:4249.
19. Cease et al. (1987), *PNAS*, 84:4249.
20. Milich et al. (1986), *J. Exp. Med.*, 164:532.
21. Kessler et al. (19660), *Hlev. Chim. Acta*, 49:1330.
22. Manning, M. (1968), *J. Am. Chem. Soc.*, 90:1348.
23. Halpern et al. (1980), *Synthetic Comm.*, 10:569.
24. Tesser et al. (1975), *Int. J. Peptide Protein Res.*, 7:295.
25. Mitchell et al. (1978). *J. Org. Chem.*, 43:2845.
26. Kloetzer et al. (1985), *Virology*, 140:230–238.
27. Laemmli (1970), *Nature*, 227:680–685.
28. Livingstone et al. (1987), *Ann.Rev. Immunol.*, 5: 477.

What is claimed is:

1. A peptidyl-resin conjugate comprising an immunogenic or antigenic peptide conjugated to a polyamide resin, the peptide incorporating a helper T-cell reactive epitope and a B-cell reactive epitope, the helper T-cell reactive epitope being positioned on the peptide distal of the B-cell reactive epitope with respect to the resin.

2. The conjugate of claim 1, wherein the helper T-cell epitope includes an amino acid sequence selected from the group of sequences consisting of:
    (a) —K—M—V—E—N—A—K—;
    (b) —D—L—Q—V—L—A—Q—K—V—A—R—R—T—L—P—(C)—;
    (c) —T—D—R—P—S—Q—Q—L—R—;
    (d) —P—S—D—K—H—I—E—Q—Y—L—K—K—I—K—N—S—I—S—;
    (e) —K—Q—I—I—N—M—W—Q—Q—V—G—K—A—M—Y—A—;
    (f) —H—E—D—I—I—S—L—W—N—Q—S—L—K—; and
    (g) —M—Q—W—N—S—T—T—F—H—Q—T—L—Q—.

3. The conjugate of claim 2, wherein the T-cell epitope includes the amino acid sequence (a) —K—M—V—E—N—A—K—.

4. The conjugate of claim 1, wherein the B-cell epitope comprises an abl epitope.

5. The conjugate of claim 1, wherein the peptide comprises from about 20 to about 50 amino acids in length.

6. The conjugate of claim 5, wherein the helper T-cell epitope comprises from about 10 to about 20 amino acids in length.

7. The conjugate of claim 1, wherein the polyamide resin is a cross-linked polydimethylacrylamide resin.

8. The conjugate of claim 1, wherein the peptide is synthesized on a polyamide resin, the peptide being coupled to the resin through a linker.

9. A method for preparing an immunogenic or antigenic peptidyl-resin conjugate, comprising the steps of:
    (a) selecting a polyamide resin; and
    (b) synthesizing onto the resin a peptide which includes a helper T-cell reactive epitope and a B-cell reactive epitope, the helper T-cell reactive epitope being positioned on the peptide distal of the B-cell reactive epitope with respect to the resin, to provide the conjugate.

* * * * *

UNITED STATES PATENT AND TRADEMARK OFFICE
CERTIFICATE OF CORRECTION

PATENT NO.    :   5,126,399

DATED         :   June 30, 1992

INVENTOR(S)   :   Ralph B. Arlinghaus of Bellaire, Texas
                  T. Sparrow of Houston, Texas It is certified that error appears in the above-identified patent and that said Letters Patent is hereby corrected as shown below:

```
    In Claim 2, line 20, column 2, of the sequence listing
delete the last "R".  The line should therefore read as
follows:

-D-L-Q-V-L-A-Q-K-V-A-R
```

Signed and Sealed this

Seventeenth Day of August, 1993

*Attest:*

BRUCE LEHMAN

*Attesting Officer*     Commissioner of Patents and Trademarks